United States Patent [19]

Lindstrom et al.

[11] Patent Number: 5,024,230

[45] Date of Patent: Jun. 18, 1991

[54] DUAL FLOW/LAMBDA DISPLAY FOR XENON ENHANCED TOMOGRAPHY

[75] Inventors: Walter W. Lindstrom, Shaker Hts.; Isaac Dinewitz, Cleveland Hts., both of Ohio

[73] Assignee: Picker International, Inc., Highland Hts., Ohio

[21] Appl. No.: 325,206

[22] Filed: Mar. 17, 1989

Related U.S. Application Data

[63] Continuation-in-part of Ser. No. 275,784, Nov. 23, 1988, which is a continuation-in-part of Ser. No. 933,781, Nov. 24, 1986, Pat. No. 4,793,357.

[51] Int. Cl.$^5$ .............................................. A61B 6/00
[52] U.S. Cl. ................................... 128/654; 128/659; 128/719; 382/6; 382/18
[58] Field of Search .................. 128/653 R, 654, 659, 128/719; 382/6, 18, 51; 364/413.13

[56] References Cited

U.S. PATENT DOCUMENTS

| | | | |
|---|---|---|---|
| 3,890,959 | 6/1975 | Youdin et al. | 128/2.05 F |
| 4,334,240 | 6/1982 | Franklin | 358/78 |
| 4,534,223 | 8/1985 | Sinha et al. | 73/703 |
| 4,535,780 | 8/1985 | Gur et al. | 128/659 |
| 4,622,976 | 11/1986 | Timpe et al. | 128/654 |
| 4,658,827 | 4/1987 | Ping He et al. | 128/660 |
| 4,710,822 | 12/1987 | Matsunawa | 382/51 |
| 4,779,621 | 10/1988 | Mattson | 128/654 |
| 4,839,807 | 6/1989 | Doi et al. | 382/6 |
| 4,922,915 | 5/1990 | Arnold et al. | 128/653 R |

FOREIGN PATENT DOCUMENTS

| | | |
|---|---|---|
| 3522113 | 1/1986 | Fed. Rep. of Germany . |
| 2161275 | 1/1986 | United Kingdom . |

OTHER PUBLICATIONS

"Regional Cerebral Blood Flow Measurements Using Stable Xenon Enhanced Computed Tomography: A Theoretical and Experimental Evaluation" by Kishore, et al., Journal of Computer Assisted Tomography, vol. 8, No. 4, 1984, pp. 619-630.

"Progress in Cerebrovascular Disease: Local Cerebral Blood Flow by Xenon Enhanced CT" by Gur, et al., Stroke, vol. 13, No. 6, 1982, pp. 750-758.

"Experimental Xenon Enhancement with CT Imaging: Cerebral Applications" by Drayer, et al., AJR: 134, Jan. 1980, pp. 39-44.

"Simultaneous Mass Spectrometry and Thermoconductivity Measurements of end-tidal Xenon Concentrations: A Comparision" by Gur, et al., Med. Phys., 11(2), Mar./Apr. 1984, pp. 209-212.

A Portable Device for the Measurement of Regional Cerebral Blood Flow in the ICU and or Using Cd Te Detectors and a Fourier Transform Based Data Analysis Corrella, et al, IEEE Transactions on Nuclear Science vol. N5-28 No. 1, Feb. 1981 pp. 50-54.

*Primary Examiner*—Ruth S. Smith
*Attorney, Agent, or Firm*—Fay, Sharpe, Beall, Fagan, Minnich & McKee

[57] ABSTRACT

A patient is disposed within a scan circle or examination region (62) of a CT scanner (B). As the patient starts breathing air from a xenon gas supply (A), a flow image and a lambda image are created and stored in a flow image memory (90) and a lambda image memory (92). The flow and lambda images, as well as a standard CT image, are displayed in quadrants of a video monitor (102). A joystick (106) enables the operator to designate a region of interest on the displayed image representations. Corresponding flow and lambda values are retrieved from the flow and lambda image memories for each spatial location or pixel within the region of interest. The flow and lambda values are loaded into a flow vs. lambda image memory (112) which is addressed in one direction by the flow values and in another by the lambda values to create a count of the flow and lambda value pairs. The information in the flow vs. lambda image memory is displayed as a histogram in one quadrant of the video display. The joystick further enables the operator to designate a section of the histogram as white matter and another portion as gray matter. A statistical analysis circuit (122) analyses the designated white matter and gray matter data to determine average flow and lambda values for each. These average flow and lambda values are displayed numerically with appropriate headings on the video display monitor.

18 Claims, 3 Drawing Sheets

DUAL FLOW/LAMBDA DISPLAY FOR XENON ENHANCED TOMOGRAPHY

The present application is a continuation-in-part of U.S. patent application Ser. No. 275,784, filed Nov. 23, 1988, which in turn is a continuation-in-part of U.S. patent application No. 933,781, filed Nov. 24, 1986, now U.S. Pat. No. 4,793,357, issued Dec. 27, 1988.

BACKGROUND OF THE INVENTION

The present invention pertains to the art of medical diagnostic imaging. It finds particular application in conjunction with xenon absorption enhanced x-ray tomographic imaging equipment and will be described with particular reference thereto. However, it is to be appreciated that the invention may also find application in conjunction with other gas absorption enhanced CT imaging techniques, other imaging modalities, and the like.

Arterial blood gas concentration is in equilibrium with lung gases that are in intimate contact with the alveoles. These lung gases, denoted as end-tidal gases, are found at the end of the tide of the exhaled breath. By measuring the concentration of a gas in question in these last bits of the exhaled air, the concentration of the gas in the blood can be determined.

The migration of xenon or other gases through the human anatomy has been measured with a series of CT scans. A first or reference CT scan of the series is taken, before xenon is introduced into the breathing gases. Second, third, and subsequent scans are taken at selected later times. The difference between the reference scan taken in the absence of xenon and the later scans is indicative of the spatial position and quantity of absorbed xenon within the patient tissue. From these difference images and the concentration of xenon in the blood as measured from the end-tidal gases, a flow value and a lambda or partition coefficient value are calculated for each pixel or voxel of the CT scan image. The flow is indicative of blood flow in imaged brain tissue and the lambda value is indicative of a partition coefficient or xenon solubility of the brain tissue. Frequently, a confidence image is also derived, which is indicative of the reliability of the flow and lambda value for each image cell based on a statistical analysis of the data from which the flow and lambda values are calculated. Techniques for determining these values are described in detail in parent U.S. Pat. No. 4,793,357, the disclosure of which is incorporated herein by reference, as well as Gur, et al U.S. Pat. No. 4,535,780, issued Aug. 20, 1985.

The data is displayed in graphic images on a video monitor. Frequently, the monitor display is divided into quadrants to display a CT image, the flow image, the lambda image, and the confidence image. Commonly, the operator defines a region of interest with a cursor or joystick on the displayed images. The system software commonly retrieves and averages each flow value within the region of interest from the flow image or each lambda value within the region of interest from the lambda image.

Anatomical homogeneity of gray and white matter over even small tissue volumes or regions of interest is the exception, not the rule. Flow, in particular, is inhomogeneous even within clearly separated gray and white matter dominant regions of the brain. For example, in the cerebral cortex, the gray and white matter regions are too intricately connected to be separated easily by the clinician.

One of the problems with this display format is that the diagnostic value of the average flow values varies with the operator's ability to accurately define an appropriate region of interest. That is, gray matter and white matter have very different flow values, typically differing by about a factor of 3. Accordingly, even a small amount of gray matter in a perceived white matter region of interest or a small amount of white matter in a perceived gray matter region of interest can radically change the average flow values. Similarly, gray matter and white matter also have different lambda values. Gray matter lambdas are typically 0.85 and white matter lambdas are typically 1.3. Accordingly, small amounts of gray matter mixed with white matter can result in an intermediate value of lambda ($0.85 < \lambda < 1.3$), not correct for either gray or white matter. Because the prior art systems do not quantify the percentage of white and gray matter within the region of interest, these inaccuracies in the flow and lambda values may lead to incorrect diagnoses and less than optimal medical treatment.

In accordance with the present invention, a new and improved diagnostic information display technique is provided.

SUMMARY OF THE INVENTION

In accordance with one aspect of the present invention, a method of displaying flow and lambda data is provided. A flow image and a lambda image are derived, each including a flow value and a partition coefficient value for each of a plurality of common spatial position addresses. A subregion of the spatial position addresses is selected and corresponding flow and lambda values retrieved. A flow value vs. lambda value representation is created which has flow value in one dimension and lambda value in a second direction. The number of each flow value/lambda value combination is indicated by magnitude or gray scale.

In accordance with a more limited aspect of the present invention, the flow value vs. lambda value representation is divided into at least two regions—one representing white matter and the other representing gray matter. The average flow and lambda values for the white matter region and the average flow and lambda values for the gray matter region are separately calculated. A display is then provided of the average flow and lambda values for gray matter in the region of interest and average flow and lambda values for white matter in the region of interest.

In accordance with another aspect of the present invention, a xenon enhanced CT apparatus is provided which includes means for performing each of the foregoing method steps.

In accordance with another more limited aspect of the present invention, a flow vs. lambda histogram is displayed.

One advantage of the present invention is that it enables diagnostic information relative to gray and white matter to be categorized separately.

Another advantage of the present invention is that it provides a more meaningful display of flow and lambda values.

Yet another advantage of the present invention is that it determines the gray and white matter lambda and flow values more accurately.

Still further advantages of the present invention will become apparent from the following detailed description.

DETAILED DESCRIPTION OF THE DRAWINGS

The invention may take form in various steps and arrangements of steps or in various parts and arrangements of parts. The drawings are only for purposes of illustrating a preferred embodiment and are not to be construed as limiting the invention.

DETAILED DESCRIPTION OF THE PREFERRED EMBODIMENT

Figure 1A:
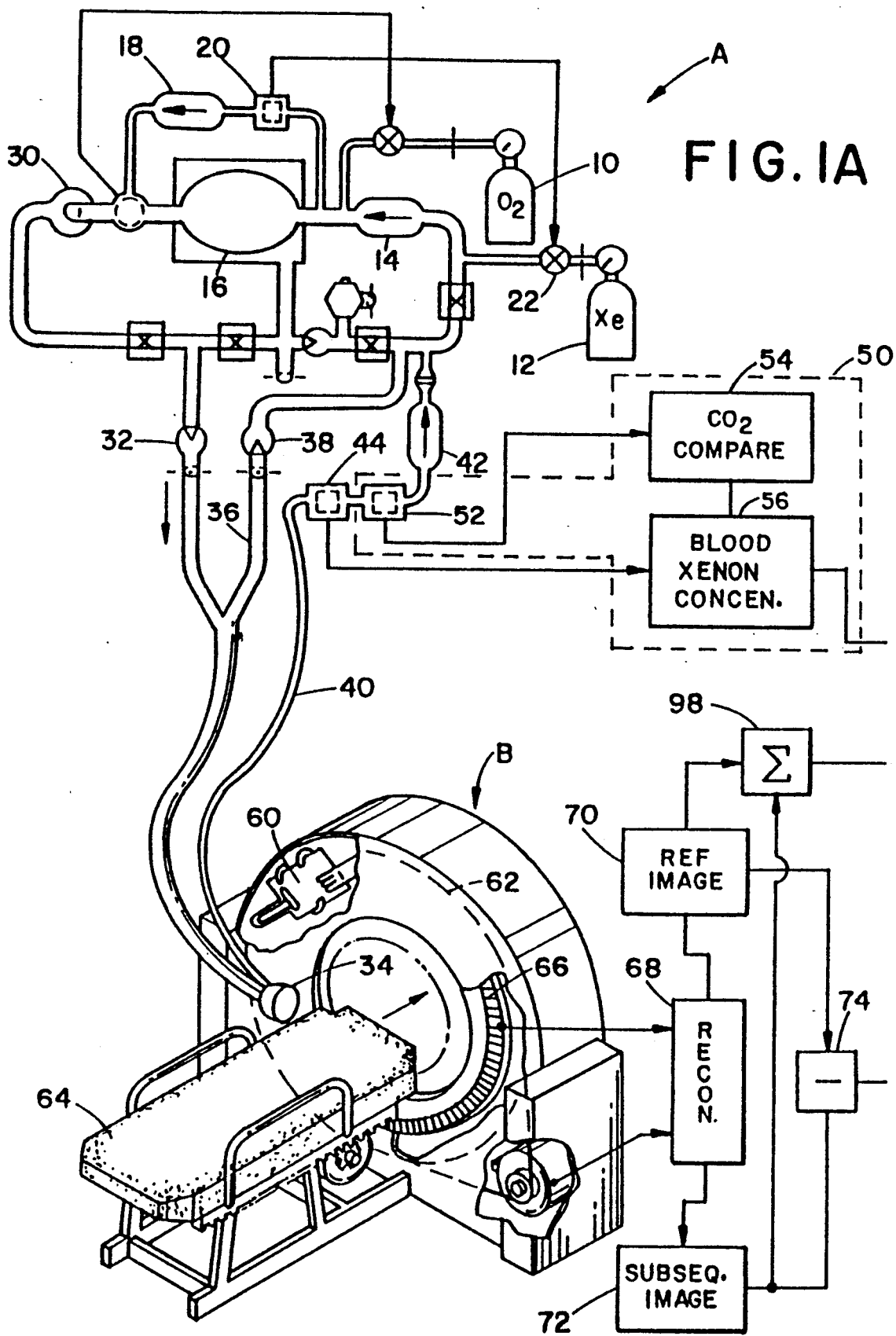
FIGS. 1A and 1B are a diagrammatic illustration of a xenon-CT system in accordance with the present invention.
Figure 1B:
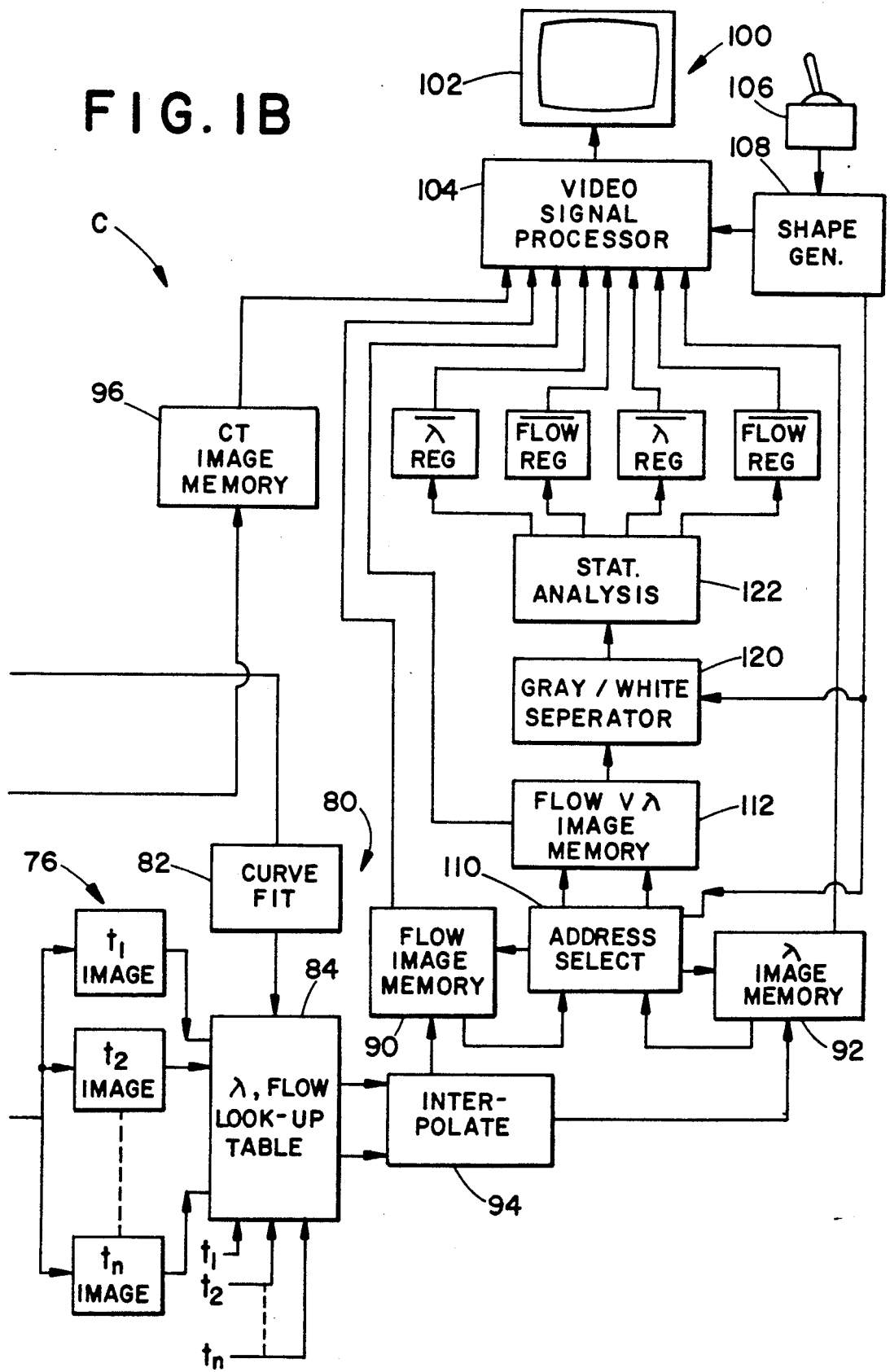

With reference to FIGS. 1A and 1B, a gas supply means A supplies breathing gas for a medical, diagnostic scanner, such as a CT scanner B. A processing system or means C processes data from the CT scanner and the breathing gas supply system to produce images and other diagnostic information.

The breathing gas supply means includes a breathing air or oxygen supply means 10 and a xenon gas supply means 12. Preferably, the xenon gas supply means provides a mixture of 80% xenon and 20% oxygen to guarantee that a patient receives at least 20% oxygen even during a malfunction. A first blower 14 supplies recirculated breathing air along with added oxygen for mixture with additional oxygen from the oxygen supply means 10. Most of the mixture passes to a breathing bag 16 with the exception of a small fraction that is pumped by a pump 18 through a xenon detector 20. The xenon detector 20 determines the concentration of xenon in the gaseous breathing mixture and controls a xenon control valve 22 to maintain the xenon concentration substantially constant. Typically, the xenon concentration is selected to be about 30%.

A carbon dioxide absorber 30 removes carbon dioxide from the breathing gases that are supplied to an outlet port check valve 32. When the patient inhales through a breathing mask 34, the patient draws the breathing gases through the outlet check valve 32. When the patient exhales, the exhaled gases are returned through an exhaust gas path or tube 36 to a return check valve 38.

A small diameter exhaust gas line 40 receives exhaust gases in parallel with exhaust tube 36. In the larger diameter exhaust tube 36, the exhaust gases tend to tumble and mix, which dilutes the end-tidal gases with other exhaust gases. The narrow diameter line inhibits the swirling and countercurrent flow patterns that tend to intermix the gases. A pump or blower 42 draws the exhaust gases through the narrow diameter exhaust line 40 and a xenon detector 44. The xenon detector measures the concentration of xenon in the exhaled gases. The exhaust gases from the return check valve 38 and from the blower 42 are recirculated to the blower 14 and the rest of the system.

An end-tidal gas detecting means 50 determines when the xenon detector 44 is measuring the concentration of xenon in end-tidal gas of each respiratory cycle. More specifically to the preferred embodiment, includes a carbon dioxide detector 52 and a carbon dioxide level comparing means 54 which compares the detected carbon dioxide level with preselected characteristics. More specifically, as the patient starts to exhale, the concentration of carbon dioxide gas increases generally exponentially and logarithmically to a plateau. The carbon dioxide concentration remains relatively constant at the plateau level through a significant portion of the exhalation portion of the respiratory cycle. At the end of the respiratory cycle, the carbon dioxide concentration drops precipitously. The carbon dioxide comparing means 54 detects the carbon dioxide concentration drop off at the end of the plateau which indicates the end-tidal portion of the respiratory cycle. The comparing means then triggers an end-tidal xenon concentration reading by a blood xenon concentration monitor 56.

A CT medical diagnostic scanner B of the preferred embodiment includes an x-ray source 60 for projecting a fan beam of radiation through an image region 62. The patient is supported on a patient table 64 with the tissue to be examined, typically the head or brain tissue, disposed in the image region. An array of x-ray detectors 66 receives the fan beam of radiation from the x-ray source including radiation which has traversed the portion of the patient in the image region. An image reconstruction means 68 reconstructs CT image representations from the x-ray data collected by the radiation detectors 66 as the radiation source 60 is rotated about the region of interest 62.

The processing circuitry includes a first or reference CT image memory means 70 for storing an image representation of the tissue in the image region without xenon gas absorbed in the patient's blood. As the patient starts inhaling xenon gas and the patient's blood xenon concentration increases, additional CT images are reconstructed. Each subsequent image is stored temporarily in a second or subsequent CT image memory 72. Each image can be considered the sum of the patient tissue image and a xenon image. A subtraction means 74 subtracts the reference image from each subsequent image to produce a difference images indicative of xenon concentrations. More specifically, each difference image includes an array of pixel values, each pixel value corresponding to a preselected volume cell (voxel) or subregion of the portion of the patient disposed in the image region. The difference images are stored in an array 76 of difference image memories.

A lambda or partition coefficient and blood flow rate determining means 80 utilizes well known relationships, such as the relationships set forth in the Kety Equation, to determine a lambda or partition coefficient and a blood flow rate for each image voxel. These calculations are based on a blood xenon concentration curve determined by a blood xenon concentration curve determining means 82 from the blood xenon concentrations measured by the blood xenon concentration means 56. In the preferred embodiment, the partition coefficient and flow values are determined on a pixel by pixel basis by a look-up table means 84. The look-up table means is addressed by the relative times $t_1, t_2, \ldots t_n$ of the CT scans, the corresponding pixel values of the plurality of difference images stored in difference image memories 76, and by the blood xenon concentration curve parameters, determined by the curve fitting means 82. More specifically, the concentration curve fitting means 82 determines conformity of the actual blood xenon concentration increase to preselected concentration curve characteristics, such as saturation concentration, slope, exponential time constants, and the like.

In one embodiment, the look-up table means 84 includes an array of look-up tables. The blood xenon concentration curve characteristics from the curve fitting means 82 determine which look-up table conforms best to the patient blood xenon concentration curve. The selected look-up table is then addressed by the corresponding pixel values from each image in the difference image memory means 76. The relative times in which the images were collected in the preferred embodiment are preset. However, if the times are to be variable, these times are also utilized to select among a larger plurality of look-up tables. More specifically, the look-up table means includes for each set of curve characteristics, an n dimensional look-up table, which is addressed by the n values corresponding to the same pixel of each of the n difference image memories 76 to retrieve a flow and lambda or partition coefficient value corresponding to each pixel value. The lambda and flow values are placed at corresponding pixel addresses of a flow image memory 90 and a lambda or partition coefficient image memory 92.

It is to be appreciated that digital look-up tables can only be addressed by preselected addresses, between which the actual pixel values may be fall. To this end, the two closest addresses may be addressed and an interpolating means 94 may perform a weighted interpolation of the received partition coefficient and flow values. Analogously, the absorption curve characteristics determined by the curve fitting means 82 may fall between two or more look-up tables of the array. The interpolation means 94 may further perform a weighted interpolation of the partition coefficient and flow values received from the look-up tables corresponding to the two closest absorption curves. This procedure is repeated for each pixel value until a complete flow and lambda image is generated and stored in the flow and lambda image memory means.

A CT image memory means 96 assembles the appropriate data from the reference and subsequent image memories 70 and 72 to provide a CT image representation of the portion of the patient in the examination region. A CT image means 98 selects which of the reference and subsequent images are loaded into the CT image memory means or averages the reference and subsequent images. Of course, if the reference image is utilized as the CT image, then the CT image memory 96 becomes redundant with the reference image memory 70 and may be eliminated.

A display means 100 includes a video monitor 102 which produces a man-readable display. A video signal processor 104 reads the image memories 90, 92, 96 and converts the image data into standard format video signals for the video monitor. The signal processor 104 arranges the image data such that the CT, flow, and lambda images are displayed concurrently in each of four quadrants of the video image. A joystick 106 controls a shape generator 108 to provide a moveable man-readable display of a region of interest concurrently on the same region of the CT, flow, and partition coefficient images. The operator with manual controls on the joystick selects the location of the region of interest, and its size and shape. For example, the region of interest may be defined by an oval whose position, size, and the relative length of its major and minor axes is selectively adjustable by the joystick.

An address selecting means 110 selects and serially outputs the flow and lambda values from the addresses which fall within the defined region of interest. Each address is supplied concurrently to the flow and partition coefficient image memories 90, 92 to retrieve the flow and partition coefficient values corresponding to each pixel within the region. The pair of retrieved partition coefficient and flow values are returned to the addressing means 110 and supplied as an address pair to a flow vs. lambda image memory means 112. The flow vs. lambda image memory means includes a two dimensional memory which is addressed in one dimension by the flow value and in the other dimension by the partition coefficient or lambda value. Each time the memory is addressed by a flow and partition coefficient address pair, the count or magnitude at the corresponding memory element is incremented. In this manner, an image representation of flow value vs. partition coefficient value is generated. The flow vs. partition function coefficient image memory means 112 is connected with the video signal processor 104 such that a flow vs. partition coefficient image is displayed in the fourth quadrant.

Figure 2:
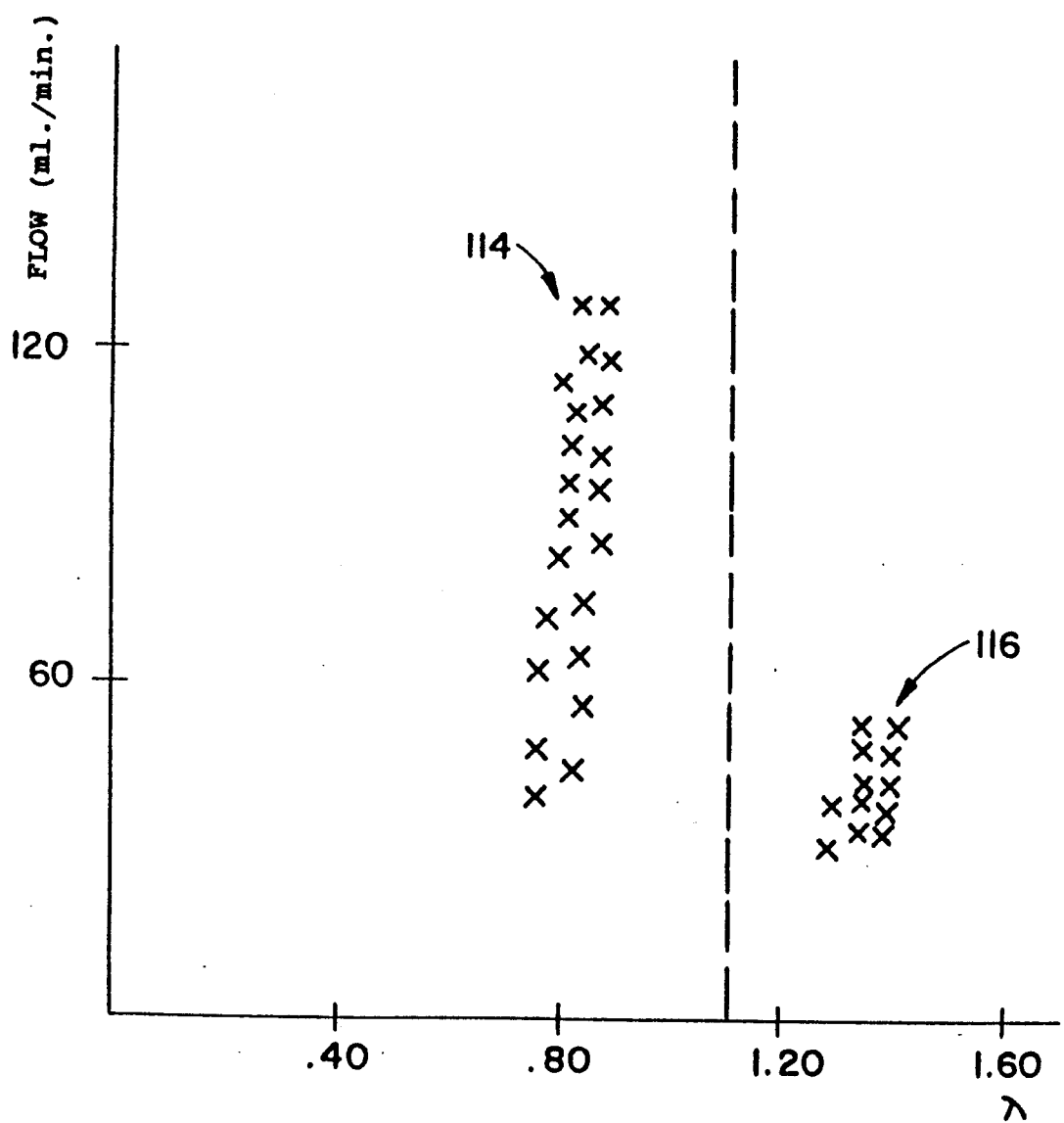
FIG. 2 illustrates a preferred flow vs. lambda value display including data values of a typical, healthy patient.

With reference to FIG. 2, a flow/lambda histogram image is displayed. The flow/lambda combinations that occur most frequently are most white, those that occur not at all, black, and those that occur less frequently with an intermediate gray tone. Due to CT image noise and tissue variability, the histogram tends to include an island of high intensity with a peripheral gray tone or lower intensity region. More specifically, a first island 114 created for the gray matter and a second island 116 for the white matter.

Typically, data in which the lambda is above 0.60 and below 1.00 are indicative of gray matter, whereas lambdas between 1.20 and 1.40 are indicative of white matter. A gray matter, white matter separating means 120 selectively addresses the data occurring with the lambda between 0.60 and 1.00 and the data from the flow vs. lambda histogram occurring with the lambda between 1.20 and 1.40. A statistical analysis means 122 analyzes these two portions of the flow vs. lambda histogram data to determine characteristics of the gray and white matter. More specifically, the statistical analysis means determines an average gray matter flow which is communicated to a gray matter flow register 124 from the portion of the data with the lambda between 0.60 and 1.00 and an average gray matter partition coefficient function which is stored in a register 126. Analogously, the statistical analysis means calculates an average white matter flow and lambda and the data for the lambda between 1.20 and 1.40 and stores these values in a white matter flow register 128 and a white matter lambda register 130. These registers are connected with the display means 100. Preferably, the average flow and lambda values with appropriate descriptive headings or captions are displayed superimposed on the display screen between actual images. Optionally, the statistical analysis means may perform other analyses of this data. For example, the statistical analysis means may determine the mean flow nd lambda value for gray and white tissue. The statistical analysis means may also determine the standard deviation or other indications of the degree of spread of these values. Other statistical analyses may also be performed.

The joystick 106 is also connected with the separating means 120 for adjusting the gray matter and white matter portions of the flow/lambda histogram. By moving the joystick, the operator can select sections of the histogram for the gray matter and/or the white matter calculations. Sections of the histogram with excessively low or high flow or lambda values may be removed from either region and discarded as dead brain tissue, system noise, or the like. The white and/or gray matter regions designated by the joystick are communicated to the display means 100 such that one or both may be framed or outlined with an accent color or tone relative to the rest of the flow vs. lambda histogram display.

The invention has been defined with reference to the preferred embodiment. Obviously, modifications and alterations will become apparent to those of ordinary skill in the art upon reading and understanding the preceding specification. It is intended that the invention be construed as including all such alterations and modifications insofar as they come within the scope of the appended claims or the equivalents thereof.

Having thus described the preferred embodiment, the invention is now claimed to be:

1. An apparatus for producing flow and partition coefficient data for gray and white matter brain tissue, the apparatus comprising:
   a flow and partition coefficient producing means for producing corresponding flow and partition coefficient values for each of a plurality of spatial locations;
   a selecting means for selecting a region of the spatial locations;
   a means for separation a pair of flow and partition coefficient values corresponding to each spatial location in the selected region into a group representing gray matter brain tissue and a group representing white matter brain tissue;
   a statistical analysis means for analyzing the flow and partition coefficient pairs for each of the gray and white matter groups to determine at least one of an average flow value for the gray matter group, an average flow value for the white matter group, and average partition coefficient value for the gray matter group, an average partition coefficient for the white matter group, a median flow value for the gray matter group, a median flow value for the white matter group, a median partition coefficient value for the gray matter group, a median partition coefficient value for the white matter group, a flow value distribution for the gray matter group, a flow value distribution for the white matter group, a partition coefficient value distribution for the gray matter group, and a partition coefficient value distribution for the white matter group.

2. The apparatus as set forth in claim 1 further including a flow vs. partition coefficient memory means which is addressable in one dimension by flow value and in a second dimension by partition coefficient value, the flow vs. partition coefficient memory means being operatively connected with the flow and partition coefficient producing means and the selecting means for storing a count of each flow and partition coefficient value pair within the selected region.

3. The apparatus as set forth in claim 2 further including:
   a flow image memory means for storing flow values corresponding to the spatial locations;
   a partition coefficient memory means for storing partition coefficient values corresponding to the spatial locations;
   a display means for displaying a man-readable flow image from the values in the flow image memory means, a partition coefficient image from the partition coefficient values of the partition coefficient image memory means, a flow vs. partition coefficient histogram from the flow vs. partition coefficient memory means, and at least one output from the statistical analysis means.

4. An apparatus for displaying flow and partition coefficient data, the apparatus comprising:
   a CT scanner;
   a gas supply means for supplying breathing gas mixed with an enhancement agent to a subject positioned in the CT scanner;
   processing means for processing data from the CT scanner and the gas supply means into flow values and partition coefficient values corresponding to each of a plurality of spatial positions;
   a flow image memory means for storing the flow values corresponding to each of the plurality of spatial positions at corresponding addresses;
   a partition coefficient image memory means for storing the partition coefficient values for each of the plurality of spatial positions at corresponding addresses;
   a means for designating a region of the spatial positions;
   a means for retrieving corresponding flow and partition coefficient values for each spatial position of the selected region with the corresponding addresses; and,
   a flow vs. partition coefficient memory means for storing magnitudes indicative of each of the plurality of retrieved flow and partition coefficient value pairs corresponding to the region of interest;
   a display means for providing a man-readable display of a histogram of the flow vs. partition coefficient pairs from the flow vs. partition coefficient memory means.

5. The apparatus as set forth in claim 4 further including a means for separating the flow vs. partition coefficient representation into at least first and second sections, the first section corresponding to gray matter brain tissue and the second section corresponding to white matter brain tissue.

6. The apparatus as set forth in claim 5 further including a statistical analysis means for determining an average flow value and an average partition coefficient for each of the first and second sections.

7. A method of displaying brain tissue flow and partition coefficient data, the method comprising:
   administering an enhancement agent to a subject in an examination region;
   measuring enhancement agent data indicative of an enhancement agent concentration in the subject and of a duration that the enhancement agent has been administered;
   irradiating a portion of the subject in the examination region and producing radiation data indicative of radiation attenuation;
   deriving from the enhancement agent data and the radiation data a flow image representation which includes a flow value for each of a plurality of spatial positions and a partition coefficient image representation which includes a partition coefficient value for each of the spatial positions;
   selecting a subregion of the spatial positions;
   for each spatial position of the subregion, retrieving a corresponding pair of flow and partition coefficient values;

creating a flow value vs. partition coefficient value representation which includes a magnitude value corresponding to a frequency with which each of the flow value and partition coefficient value pairs are retrieved;

displaying a man-readable histogram of the flow value vs. partition coefficient value representation.

8. The method as set forth in claim 7 further including dividing the flow value vs. partition coefficient value representation into at least two sections, one section corresponding to gray matter brain tissue and a second section corresponding to white matter brain tissue.

9. The method as set forth in claim 8 further including manually adjusting the first and second sections in accordance with the histogram display.

10. The method as set forth in claim 8 further including calculating an average flow value for each of the first and second sections.

11. The method as set forth in claim 10 further including calculating an average partition coefficient value for each of the first and second sections.

12. The method as set forth in claim 11 further including generating a man-readable display of the average flow value of gray and white matter and the average partition coefficient values of gray and white matter.

13. The method as set forth in claim 12 further including providing a man-readable display of the flow image representation and the partition coefficient image representation.

14. A method of producing flow and partition coefficient values, the method comprising:

administering an enhancement agent mixed with breathing gases to a subject in an examination region;

producing enhancement agent data indicative of enhancement agent concentration and times of administration;

irradiating a portion of the subject in the examination region and generating radiation data indicative of radiation traversing the irradiated patient portion;

generating flow and partition coefficient image representations from the enhancement agent data and the radiation data;

selecting corresponding regions of the flow image representation and the partition coefficient image representation which include a plurality of corresponding flow and partition coefficient values;

sorting each pair of corresponding flow and partition coefficient values on the basis of the partition coefficient value into at least two groups;

determining an average flow value for each of the two groups.

15. The method as set forth in claim 14 further including determining an average partition coefficient for each of the two groups.

16. The method as set forth in claim 15 further including creating a flow value vs. partition coefficient value representation for the flow value and partition coefficient value pairs retrieved from the selected corresponding regions.

17. The method as set forth in claim 16 further including displaying on a common man-readable display the flow image representation, the partition coefficient image representation, the flow value vs. partition coefficient value representation, a designation of the selected region, the average flow value for the selected region, and the average partition coefficient value for the selected region.

18. A method for producing flow and partition coefficient information displays for gray and white matter brain tissue, the method comprising:

producing pairs of flow and partition coefficient values each pair corresponding to one of a plurality of spatial locations;

selecting a subregion of the spatial locations;

separating the pairs of flow and partition coefficient values corresponding to the spatial locations in the selected region into a first group representing gray matter brain tissue and a second group representing white matter brain tissue;

analyzing the flow and partition coefficient pairs of the first and second groups to determine at least one of: an average flow value for the first group, an average flow value for the second group, an average partition coefficient value for the first group, an average partition coefficient value for the second group, a median flow value for the first group, a median flow value for the second group, a median partition coefficient value for the first group, a median partition coefficient value for the second group, a flow value distribution for the first group, a flow value distribution for the second group, a partition coefficient value distribution for the first group, and a partition coefficient value distribution for the second group;

selectively displaying at least one of a flow image indicative of flow value vs. spatial location, a partition coefficient image indicative of partition coefficient value vs. spatial position, the average flow value for the first group, the average flow value for the second group, the average partition coefficient value for the first group, the average partition coefficient value for the second group, the median flow value for the first group, the median flow value for the second group, the median partition coefficient value for the first group, the median partition coefficient value for the second group, the flow value distribution for the first group, the flow value distribution for the second group, the partition coefficient distribution for the first group, and the partition coefficient distribution for the second group.

* * * * *